United States Patent [19]

Helenowski

[11] Patent Number: 5,084,045

[45] Date of Patent: Jan. 28, 1992

[54] SUCTION SURGICAL INSTRUMENT

[76] Inventor: Tomasz K. Helenowski, 936 Burnham Ct., Glenview, Ill. 60025-4140

[21] Appl. No.: 583,194

[22] Filed: Sep. 17, 1990

[51] Int. Cl.$^5$ ............................................. A61N 1/02
[52] U.S. Cl. ...................................... 606/32; 606/48; 606/49
[58] Field of Search ................ 606/27, 28, 29, 32, 606/41, 48, 49, 50

[56] References Cited

U.S. PATENT DOCUMENTS

| | | | |
|---|---|---|---|
| 1,916,722 | 7/1933 | Ende | 606/50 |
| 1,943,543 | 1/1934 | McFadden | 606/49 |
| 2,888,928 | 6/1959 | Seiger | 606/49 |
| 4,483,338 | 11/1984 | Bloom et al. | 606/50 |
| 4,719,914 | 1/1988 | Johnson | 606/28 |
| 4,832,048 | 5/1989 | Cohen | 606/41 |
| 4,919,129 | 4/1990 | Weber, Jr. et al. | 606/49 X |
| 4,932,952 | 6/1990 | Wojciechowicz, Jr. | 606/49 |

FOREIGN PATENT DOCUMENTS

84/03829 10/1984 World Int. Prop. O. ............ 606/49

*Primary Examiner*—Robert A. Hafer
*Assistant Examiner*—Sam Rimell

[57] ABSTRACT

A surgical instrument consisting of three concentric tubes, with the outer and inner tubes made of electrical current conducting material which are in turn connected to a bipolar current generator. When the tips of such tubes are placed against tissue a current will flow therebetween and cauterize such tissue. To prevent short circuiting between the two conductive tips the third or middle tube constitutes an insulator. A suction tube equipped with a suction regulator is integral with the instrument and has open communication with the current conductive tips which are designed to be longitudinally separated by an open slot that allows continuous air flow therebetween and into the suction tube during the surgical procedure.

16 Claims, 2 Drawing Sheets

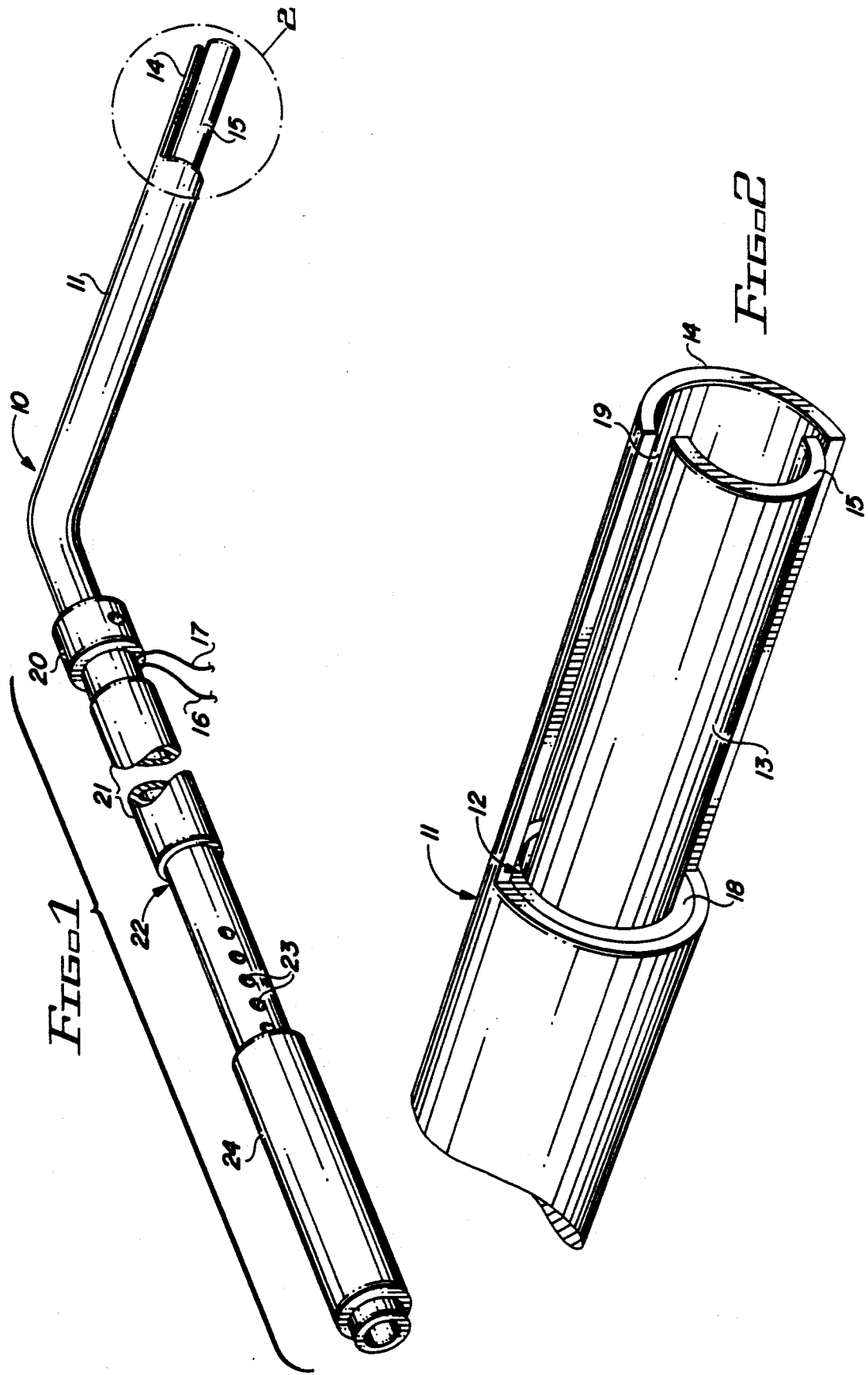

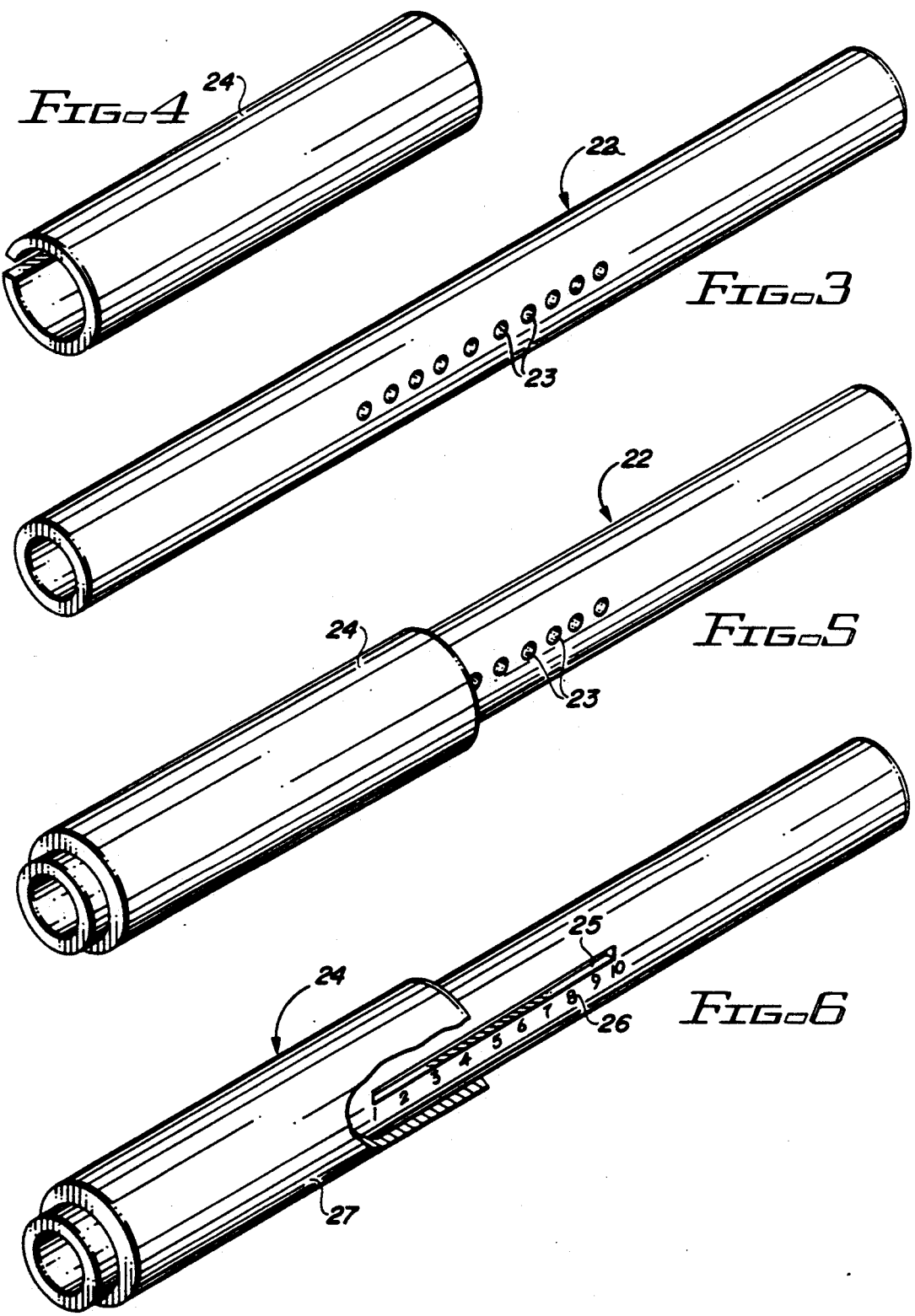

SUCTION SURGICAL INSTRUMENT

FIELD OF INVENTION

The present invention relates to a surgical instrument having an evacuating system for drawing off liquids, tissue and plumes from the surgical field. The instrument provides a cauterizing tip consisting of insulated current conductive tube ends, in open communication with a suction tube that can duplicate the selected relative degree or magnitude of suction during the surgical procedure.

The instrument of this invention is particularly useful in laser surgery with the cauterizing tips used as a tissue retractor for the laser surgical field. The evacuation system will remove all laser plumes during such operation.

DESCRIPTION OF THE PRIOR ART

Conventional suction surgical instruments employ tubular suction shafts of metal which are costly to produce. In such instruments the electrical conductivity of the metallic suction shafts serve to connect the same to a source of high frequency current used for the purpose of cauterizing the tissue. In these prior devices the tissue becomes cauterized and coagulated not only at the desired location in the operating area but also deeper within the tissue. The previous suction cautery devices are "monopolar" with a distant grounding plate. This allows the current to flow through the tip to the tissues to deeper levels since the current flows from the tip to the grounding plate.

It is the purpose of the present invention to obviate the aforementioned difficulties by providing a regulated suction surgical instrument which will remain unobstructed when employed as a cauterizing instrument, and provide a more controlled cauterizing current which flows between the closely spaced tips.

SUMMARY OF THE INVENTION

The preferred embodiment of the present invention provides a suctioned cauterizing instrument that is simple in manufacture, economical and highly effective in use.

The instrument consists of a cauterizing tip in open communication with a disposable suction tube. The cauterizing tip is constructed from three concentric tubes with the outer and inner tubes made from electrical current conducting material. These tubes are in turn connected to a bipolar current generator. The middle tube functions as an insulator preventing electrical short circuiting between the outer and inner conducting tubes. To assure continuous suctioned air flow within the cauterizing tip the inner and outer tubes are arranged so as to provide an open slot therebetween. This open slot prevents clogging by any retracted and cauterized tissue and allows fluid and plume to be evacuated from the surgical field.

The suction regulator is constructed from a flexible material and is provided with a series of holes cut along the length thereof. An occluder in the form of a C-shaped flexible cover tubing is then placed over the area in which the holes have been cut. As the occluder is moved along the length of the suction tube so as to seal off a determined number of holes, the degree of suction will be reproducibly regulated.

DESCRIPTION OF THE DRAWINGS

This invention will be best understood by reference to the accompanying drawings which illustrate the preferred form of construction and arrangement of parts by which the objects of the invention are achieved, and in which FIG. 1 is a perspective view of the surgical instrument of this invention, FIG. 2 is a fragmentary enlarged view of the surgical tip of this invention, FIG. 3 is a fragmentary perspective view of the suction regulator, FIG. 4 is a fragmentary perspective view of the suction regulator occluder, FIG. 5 is a fragmentary perspective view of the composite suction regulator, and FIG. 6 is fragmentary perspective view of a modified suction regulator adaptable for use with the surgical instrument.

DESCRIPTION OF THE INVENTION

As illustrated in FIG. 1 the surgical instrument 10 of this invention consists of three concentric coaxial tubes 11, 12 and 13. The outer tube 11 as well as the inner tube 13 provides longitudinal extensions which form surgical tips 14 and 15.

The tubes 11 and 13 are made from any highly conductive material, or can have conductive wires implanted in a non-conductive material such as any suitable plastic or the like with the wire leads providing an exposed end.

The surgical tips 14 and 15 are adapted to be connected to a bipolar generator as a source of electrical current by leads 16 and 17, such that when the tips 14 and 15 are pressed against tissue, and the current is on, an electrical charge will flow between the tips 14 and 15 and cauterize the adjacent tissue.

To prevent shorting of the surgical tips 14 and 15 as well as the tubes 11 and 13, if they are fabricated from conductive material, an insulator 18 extends concentrically coaxially thereof.

As shown the surgical tips 14 and 15 are semi-circular in cross section and disposed in parallel spaced confronting relation. By this arrangement an elongated open channel 19 is formed between the tips 14 and 15. This channel 19 allows continuous air flow between the surgical tips 14 and 15 when they are placed against and caused to cauterize the tissue. This open channel 19 will also evacuate the plume and other debris and fluids from the surgical field.

A suitable insulated handle or cover 20 is incorporated onto the body 11 facilitating its use and insulating the user from any electrical shock.

An elongated section of flexible tubing 21 extends between the handle 20 and a suction regulator 22. The length of the tubing 21 permits physical spacing between the surgeon working the instrument and an assistant nurse who operates the suction activities of the instrument.

FIG. 3 illustrates a suction regulator 22 fabricated from any suitable non-conductive material, preferably one from the plastic family. Along a portion of its length a series of holes 23 are formed to provide open communication with the interior of the regulator 22. A C-shaped occluder 24 is adapted to fit over the regulator 22 so as to be slidably mounted thereon. By sliding the occluder 24 over the regulator 22 a selected number of holes 23 may be closed, thereby regulating the strength or volume of the suction in the regulator 22. The holes 23 may be identified by reference indicia, such as by numbers, whereby the selected strength or volume of the suction may be reproducibly obtained during subsequent surgical procedures.

The regulator 22 as described herein may be an appendage to any existing disposable suction tubing which is currently used, or may be a disposable insertable section to such system. The regulator 22 of this invention may be operatively connected in any suitable manner to a vacuum creating source, such as a blower or the like.

FIG. 5 illustrates a modified suction regulator 24 wherein it is constructed from a rigid material. Through the use of a rigid material a regulating slot 25 may be cut in one wall thereof, with the slot bearing throughout its length informational indicia 26. The regulator 24 if not constructed from a rigid material would by reason of the elongated cut slot 25 collapse inwardly under suction thereby rendering it inoperative. A occluder 27 is employed and operates in an identical manner to that previously described.

From the foregoing it is apparent that I have devised a suction surgical instrument having novel electrical conductive cauterizing tips operable in conjunction with a regulated suction recovery system. The suction surgical instrument of this invention may be appended to existing suction systems and be a part of the disposable portions thereof.

While I have illustrated and described the preferred form on construction for carrying my invention into effect, this is capable of variation and modification without departing from the spirit of the invention. I therefore, do not wish to be limited to the precise details of construction as set forth, but desire to avail myself of such variations and modifications as come within the scope of the appended claims.

Having thus described my invention what I claim as new and novel and desire to protect by Letters Patent is:

1. A suction surgical instrument comprising:
   a) a tubelike surgical body having concentrical outer and inner tubular members,
   b) an insulator extending between and coaxially of said inner and outer tubular members,
   c) said outer tubular member having a free end extending coaxially of said body and beyond said insulator so as to provide an elongated surgical tip,
   d) said inner tubular member having a free end extending coaxially of said body and beyond said insulator so as to provide a second elongated surgical tip disposed in parallel relation with said surgical tip of said outer tubular member,
   e) said elongated surgical tips of said outer and inner tubular members being longitudinally spaced so as to provide throughout their lengths open passages therebetween in open communication with said tubelike surgical body,
   f) an electric current source for said surgical tips with said current adapted to flow therebetween and through the tissue to be cauterized, and
   g) a vacuum tube in open communication with said tubelike surgical body so as to evacuate fluids through said body and throughout said open passages between said elongated surgical tips.

2. A suction surgical instrument as defined by claim 1 wherein said surgical tips are semi-circular in cross section and disposed in spaced confronting relation.

3. A suction surgical instrument as defined by claim 1 wherein said surgical tips are made from electric current conductive material.

4. A suction surgical instrument as defined by claim 3 wherein said surgical tips are semi-circular in cross section and disposed in spaced confronting relation.

5. A suction surgical instrument as defined by claim 1 including means for regulating the volume flow of vacuum through said body and said open passage between said surgical tips.

6. A suction surgical instrument as defined by claim 5 wherein said surgical tips are semi-circular in cross section and disposed in spaced confronting relation.

7. A suction surgical instrument as defined by claim 5 wherein said surgical tips are made from electric current conductive material.

8. A suction surgical instrument as defined by claim 5 wherein said surgical tips are made from electric current conductive material and are semi-circular in cross section and are disposed in parallel spaced confronting relation.

9. A suction surgical instrument as defined by claim 1 wherein said electric current source comprises a bipolar generator.

10. A suction surgical instrument as defined by claim 9 wherein said surgical tips are semi-circular in cross section and disposed in spaced confronting relation.

11. A suction surgical instrument as defined by claim 9 wherein said surgical tips are made from electric current conductive material.

12. A suction surgical instrument as defined by claim 9 wherein said surgical tips are made from electric current conductive material and are semi-circular in cross section and are disposed in parallel spaced confronting relation.

13. A suction surgical instrument as defined by claim 9 including means for regulating the volume flow of vacuum through said body and said open passages between said surgical tips, including a regulator slideable axially over said tubelike surgical body.

14. A suction surgical instrument as defined by claim 13 wherein said surgical tips are semi-circular in cross section and disposed in spaced confronting relation.

15. A suction surgical instrument as defined by claim 13 wherein said surgical tips are made from electric current conductive material.

16. A suction surgical instrument as defined by claim 8 wherein said electric current source comprises a bipolar generator.

* * * * *